United States Patent
Hock et al.

(10) Patent No.: US 6,277,961 B1
(45) Date of Patent: Aug. 21, 2001

(54) STABLE FIBRINOGEN SOLUTION

(75) Inventors: Johann Hock, Marburg; Hermann Karges, Marburg-Michelbach, both of (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 08/272,281

(22) Filed: Jul. 8, 1994

Related U.S. Application Data

(63) Continuation of application No. 08/003,318, filed on Jan. 12, 1993, now abandoned.

(30) Foreign Application Priority Data

Jan. 29, 1992 (DE) .................................................. 42 02 667

(51) Int. Cl.$^7$ .................................................. A61K 38/36
(52) U.S. Cl. .......................... 530/382; 530/381; 530/383; 530/384; 424/529; 424/94.64; 514/2
(58) Field of Search ................. 424/529, 94.64; 530/381, 382, 383, 384; 514/2; 435/183

(56) References Cited

U.S. PATENT DOCUMENTS

| | | | |
|---|---|---|---|
| 3,849,252 | * 11/1974 | Percs et al. | 424/94.64 |
| 4,170,590 | * 10/1979 | Stephen et al. | 106/112 B |
| 4,272,523 | * 6/1981 | Kotitschke et al. | 530/383 |
| 4,543,210 | * 9/1985 | Mita et al. | 530/383 |
| 4,627,879 | * 12/1986 | Rose et al. | 106/124 |
| 4,743,680 | * 5/1988 | Mathews et al. | 530/383 |
| 4,818,291 | * 4/1989 | Iwatsuki et al. | 106/124 |
| 4,847,362 | * 7/1989 | Mathews et al. | 530/384 |
| 4,960,757 | 10/1990 | Kumpe et al. | 514/21 |
| 5,099,003 | * 3/1992 | Kotitschke et al. | 530/382 |
| 5,252,709 | * 10/1993 | Burnouf et al. | 530/382 |

FOREIGN PATENT DOCUMENTS

| | | |
|---|---|---|
| 0 014 333 | 8/1980 | (EP) . |
| 0 085 923 A1 | 8/1983 | (EP) . |
| 0 103 196 | 3/1984 | (EP) . |
| 0 103 196 A2 | 3/1984 | (EP) . |
| 0 305 243 | 3/1989 | (EP) . |
| 0 311 950 | 4/1989 | (EP) . |
| 8912065 | * 12/1989 | (FR) . |
| 0416983 | * 3/1991 | (FR) . |
| WO 86/01814 | 3/1986 | (WO) . |

OTHER PUBLICATIONS

Nadkarni, G.D., et al., "Indian J. Biochem.," vol. 5 (1), 1968, p. 16–18.*

McManama, G., et al., "Blood," vol. 68(2), 1986, p. 363–371.*

Lawrie, J.S.. et al., Biochemical Society Transactions, vol. 7(4), Aug. 1979, p. 693–694.*

Suzuki:, K.. et al., "A Simple Technique for Purification of Fibrinogen from Plasma by Affinity Chromatography on ristocetin–agarose." (cited of interest).*

Nadkari, G.D.. et al., Indian J. Biochem., vol. 5(1), p. 16–18, 1968.*

English language abstract of European Patent Application No. 0 305 243 (Mar. 1, 1989).

* cited by examiner

*Primary Examiner*—Jean C. Witz
(74) *Attorney, Agent, or Firm*—Finnegan, Henderson, Farabow, Garrett and Dunner, L.L.P.

(57) ABSTRACT

A fibrinogen solution which is suitable for use in a tissue adhesive and can be stored at temperatures between +4° C. and +25° C. for at least four weeks without loss of its ability to function, in particular without significant change in consistency and coagulation properties, and a process for the preparation thereof.

12 Claims, No Drawings

STABLE FIBRINOGEN SOLUTION

This application is a continuation application of Ser. No. 08/003,318 filed Jan. 12, 1993, now abandoned.

The invention relates to a fibrinogen solution which is suitable for use in a tissue adhesive and can be stored at temperatures between +4° C. and +25° C. for at least four weeks without loss of its ability to function, in particular without significant change in consistency and coagulation properties.

Fibrin has been used for gluing tissues and for stopping bleeding for a long time. It is employed, for example, for sealing large-area bleeding, for uniting tissue in parenchymal organs, for conjuctival bonding or for securing sutures and stopping bleeding after various surgical interventions. The essential advantage compared with other methods (for example bonding with synthetic tissue adhesives) is the use of physiological substances which have high biocompatibility and a beneficial effect on wound healing. In tissue bonding, the final phase of blood coagulation is imitated: fibrinogen, which contains factor XIII, is brought into contact with thrombin and calcium ions on the area to be bonded. Thrombin cleaves the fibrinopeptides A and B from fibrinogen, resulting in fibrin monomers which form a soluble fibrin clot. At the same time, the transglutaminase factor XIII is activated by thrombin and calcium ions, and it stabilizes the clot by crosslinking the fibrin monomers. An increased resistance of the clot to fibrinolysis can be achieved if required by adding a plasmin inhibitor to the fibrinogen or thrombin solution.

On the one hand commercial products are available for tissue bonding with fibrin adhesives, and on the other hand it is also possible for the user to prepare fibrin adhesives as required (WO 86/01814).

The commercially obtainable fibrin adhesives are two-component adhesives in which the first component contains fibrinogen, factor XIII and aprotinin, and the second contains thrombin and calcium ions. The components are in either deep-frozen or freeze-dried form. One disadvantage of these products is the need to prepare the adhesive ready for use, since both the thawing and warming to the use temperature, and the dissolving of the lyophilisates take, owing to the high fibrinogen concentration of about 6–10%, a relatively long time. Another considerable disadvantage is the relatively short stability (about 4 hours) of the adhesive components ready for use. If there are unenvisaged delays between preparation and use, the fibrin adhesive can thus become unusable or lose efficacy.

Fibrinogen concentrates can also be prepared as required by the user himself, by various methods, and combined with commercially obtainable thrombin products to give a tissue adhesive. This procedure is, however, associated with the following serious disadvantages: in order to rule out the transmission of viruses, it is possible to use only blood from the patient to be treated for obtaining the fibrinogen concentrate. Since the preparation of the concentrate is labor-intensive and time-consuming, application is not possible in cases of emergency. Furthermore, a constant composition and quality of the fibrinogen concentrate is not ensured when blood from a single donor is used.

Because of the stated disadvantages both of the commercial fibrinogen concentrates and of those prepared by the user himself, there is a need for a fibrinogen concentrate which has maximum stability in the form ready for use (thawed or dissolved). The fibrinogen concentrate according to the invention eliminates both the disadvantages of previous tisse adhesives. One advantage is more rapid availability because no time needs to be spent thawing or dissolving the fibrinogen component. Another advantage is that the dissolved fibrinogen component remains able to function over a lengthy period and does not have to be discarded if an intended bonding is not carried out.

The object of the invention is therefore to provide a fibrinogen concentrate which can be stored at +4° C. to +25° C. for at least 4 weeks without loss of the ability to function. In particular a solution of this type should be useful as a component of a tissue adhesive.

EP 0,103,196 describes the preparation of a fibrinogen concentrate from cryoprecipitate which, after thawing and dilution, has been treated with 2.5% $Al(OH)_3$. The concentrate is freeze-dried for stabilization and is stable for 4 h after reconstitution.

EP 0,085,923 describes the preparation of an arginine-containing fibrinogen concentrate which remains stable for a working day.

Surprisingly, a process for preparing a fibrinogen solution which can be stored for a lengthy period with negligible loss of coagulability and thus of its suitability for tissue bonding has now been found. The process comprises subjecting a fibrinogen solution to at least two adsorption steps.

A solution treated in this way can be stored for a lengthy period without losing its ability to function even after thawing from the deep-frozen state or after dissolving from the freeze-dried state.

The invention therefore relates to a fibrinogen solution which can be stored at temperatures between +4° C. and +25° C. for at least four weeks without losing its ability to function, and which can be obtained by treating a fibrinogen solution at least twice with an adsorbent, and obtaining the supernatant each time.

A solution of a cryoprecipitate can be used as fibrinogen solution. A solution of this type can contain 1.5–15%, preferably 5–11%, of coagulable plasma protein.

Adsorbents which can be used are alkaline earth metal salts which are sparingly soluble in water or, preferably, aluminum hydroxide or ion exchangers, preferably anion exchangers.

The concentration of the alkaline earth metal salt or aluminum hydroxide for the adsorption is between 0.05 and 2.5% (weight/volume), preferably 0.05–0.5% (weight/volume), and the amount of ion exchanger used is 0.5–20g, preferably 3–10 g, per kg of cryoprecipitate.

The fibrinogen solution can, if necessary, be further purified by processes known to the person skilled in the art (for example EP 0,103,196). The fibrinogen solution obtained in this way can be stored as liquid or can be deep-frozen or freeze-dried. The fibrinogen solution or a fibrinogen solution obtained after a frozen solution or after dissolving for a freeze-dried solution can be stored at a temperature from +1° C. to +37° C. Storage is preferably at a temperature from +4° C. to +25° C. A solution according to the invention is stable for at least four weeks.

A stable solution of this type can be used as a component of a fibrin adhesive.

It can contain 10–200, preferably about 60, units of factor XIII.

The following examples illustrate the invention:

Example 1

Preparation of a Fibrinogen Concentrate

Cryoprecipitate from citrate plasma was dissolved in isotonic saline (2.8 l/kg). Subsequently, 5% (volume/volume) of an aluminum hydroxide suspension (1.5% weight/volume) was added, and the mixture was stirred for 15 min. The aluminum hydroxide was removed by centrifugation, and the same amount of aluminium hydroxide plus 5.25 g of QAE-Sephadex A-50 per kg of cryoprecipitate, was again added to the supernatant.

Centrifugation was repeated. Glycine was added to the supernatant with stirring until the final concentration was 2.7 mol/l, and the resulting precipitate was removed by centrifugation and dissolved in isotonic saline (1.5 l/kg). The solution was mixed with glycine (final concentration 1.15 mol/l) and stirred for 30 min. This was followed by centrifugation, and the residue was discarded. The supernatant was mixed with glycine (final concentration 2.15 mol/l) and stirred for 30 min. The precipitate was removed by centrifugation, taken up in 0.05 mol/l NaCl, 0.005 mol/l trisodium citrate, 0.02 mol/l arginine, pH 7.5, and dialyzed against the same buffer.

Example 2
Preparation of a Factor XIII-containing Fibrinogen Concentrate

The fibrinogen concentrate from Example 1 was mixed with 20 U/ml factor XIII from plasma and 3.3 mg/ml human albumin. The solution was adjusted to an optical density (280 nm) of 35–37 and freeze-dried.

Example 3
Stability of Factor XIII-containing Fibrinogen Concentrates in Solution at +4–8° C.

Freeze-dried fibrinogen concentrates were dissolved in 1 ml of a solution of 1000 KIU/ml aprotinin in physiological saline and stored at +4–8° C. The concentration of coagulable fibrinogen was determined by the Clauss assay, and the factor XIII activity was determined using a chromogenic assay ($^R$Berichrom factor XIII).

|  | A | | B | |
|---|---|---|---|---|
| Days | Fgn[1] | F XIII[2] | Fgn | F XIII |
| 0 | 100 | 64 | 101 | 10.3 |
| 2 | 101 | 55 | 61 | 9.2 |
| 6 | 109 | 59 | solid[3] | solid |
| 15 | 108 | 61 | | |
| 18 | 86 | 56 | | |
| 26 | 91 | 61 | | |
| 30 | 88 | 58 | | |

A Fibrinogen concentrate from Example 1 with plasma factor XIII
B Non-adsorbed cryoprecipitate as fibrinogen concentrate
[1] Fibrinogen (mg/ml)
[2] Factor XIII (U/ml)
[3] No longer liquefies on warming Example 4
Stability of Factor XIII-containing Fibrinogen Concentrate in Solution at +20° C.

A freeze-dried fibrinogen concentrate according to the invention was dissolved in 1 ml of a solution of 1000 KIU/ml aprotinin in physiological saline solution and stored at +20° C. The concentration of coagulable fibrinogen was determined by the Clauss assay, and the factor XIII activity was determined using a chromogenic assay ($^R$Berichrom factor XIII).

| Days | Fgn[1] | F XIII[2] |
|---|---|---|
| 0 | 80 | 65 |
| 2 | 87 | 65 |
| 4 | 89 | 66 |
| 9 | 86 | 63 |
| 18 | 88 | 62 |
| 22 | 62 | 71 |
| 32 | 84 | 61 |

[1] Fibrinogen (mg/ml)
[2] Factor XIII (U/ml)

What is claimed is:

1. A processed stable fibrinogen solution, obtained by a) treating a starting fibrinogen solution at least twice with an adsorbent selected from the group consisting of an anion exchanger, a sparingly soluble salt of an alkaline earth metal and aluminum hydroxide, b) removing said adsorbent from the treated fibrinogen solution leaving a supernatant, wherein the fibrinogen remains in said supernatant and c) recovering said supernatant, wherein the fibrinogen in the supernatant maintains its ability to function when stored at 4–25° C. for four weeks.

2. A processed stable fibrinogen solution as claimed in claim 1, wherein said starting fibrinogen solution is a solution of a cryoprecipitate.

3. The processed stable fibrinogen solution as claimed in claim 1, wherein the starting fibrinogen solution contains 1.5–15% of a coagulable plasma protein.

4. A processed stable fibrinogen solution as claimed in claim 1, where the amount of the alkaline earth metal salt or aluminum hydroxide for the adsorption is between 0.05 and 2.5% (weight of adsorbent/volume of starting fibrinogen solution).

5. A processed stable fibrinogen solution as claimed in claim 2, where the anion exchanger is employed in an amount of 0.5–20 g per kg of cryoprecipitate employed.

6. A processed stable fibrinogen solution as claimed in claim 1, which contains 10–200 units of factor XIII per ml of solution.

7. A process for preparing a concentrated fibrinogen solution which contains 1.5–15% of coagulable plasma protein which comprises dissolving a fibrinogen-containing starting material, treating the solution with an adsorbent at least twice, using the same or a different adsorbent, wherein the adsorbent is selected from the group consisting of an anion exchanger, a sparingly soluble salt of an alkaline earth metal and aluminum hydroxide, and removing said adsorbent from the treated fibrinogen solution leaving a supernatant wherein the fibrinogen remains in said supernatant and recovering said supernatant, wherein the fibrinogen in the supernatant maintains its ability to function when stored at 4–25° C. for four weeks.

8. A fibrin adhesive obtained by combining the processed stable fibrinogen solution as claimed in claim 1 with a thrombin solution.

9. The processed stable fibrinogen solution as claimed in claim 1, wherein the starting fibrinogen solution contains 5–11% of a coagulable plasma protein.

10. The processed stable fibrinogen solution as claimed in claim 1, where the amount of the alkaline earth metal salt or aluminum hydroxide for the adsorption is between 0.05%–0.5% (weight of adsorbent/volume of starting fibrinogen solution).

11. The processed stable fibrinogen solution as claimed in claim 2, wherein the anion exchanger is employed in an amount of 3–10 g per kg of cryoprecipitate employed.

12. The processed stable fibrinogen solution as claimed in claim 1 which contains 60 units of factor XIII per ml of solution.

* * * * *